(12) United States Patent
Borody

(10) Patent No.: US 6,277,836 B1
(45) Date of Patent: Aug. 21, 2001

(54) METHODS AND COMPOSITIONS FOR TREATING INFLAMMATORY BOWEL DISEASE

(76) Inventor: Thomas Julius Borody, 144 Great North Road, Five Dock (AU), NSW 2046

(*) Notice: Subject to any disclaimer, the term of this patent is extended or adjusted under 35 U.S.C. 154(b) by 0 days.

(21) Appl. No.: 09/381,960

(22) PCT Filed: Apr. 1, 1998

(86) PCT No.: PCT/AU98/00222

§ 371 Date: Nov. 17, 1999

§ 102(e) Date: Nov. 17, 1999

(87) PCT Pub. No.: WO98/43667

PCT Pub. Date: Oct. 8, 1998

(30) Foreign Application Priority Data

Apr. 1, 1997 (AU) .................................. PO 5940
Oct. 14, 1997 (AU) .................................. PO 9785

(51) Int. Cl.[7] .......................... A61K 31/60; A61K 31/70; A61K 31/47; A61K 31/445; A61K 31/42
(52) U.S. Cl. .............................. 514/159; 514/29; 514/34; 514/312; 514/315; 514/317; 514/374
(58) Field of Search .................... 514/159, 312, 514/315, 317, 34, 374, 29; 424/93.1

(56) References Cited

U.S. PATENT DOCUMENTS 4,440,763 * 4/1984 Lover ................................... 514/159

OTHER PUBLICATIONS

Kohn et al., "Antimycobacterial therapy in Crohn's disease: Results of a controlled, double–blind trial with a multiple antibiotic regimen", American Journal of Gastroenterology (1994) vol. 89, No. 4, 513–518.*

Rastogi, N., et al., Antimicrobial Agents and Chemotherapy, vol. 36, No. 12, pp 2843–2846 (1992).

Chiodini, R. J., et al., Antimicrobial Agents and Chemotherapy, vol. 26(6), 930–932 (1984).

Shafran, S. D., et al., The New England Journal of Medicine, vol. 335 No. 6, 377–383, 8/96.

Yajko, D. M., et al., Antimicrobial Agents and Chemotherapy, vol. 40, No. 3, 743–749, 3/96.

Pradhan, S. N., et al., Pharmacology and Medicine: Principles and Practice, SP Press International, Inc., Bethesda, Md., 1986, pp 847–858.

Berkow, R., et al., The Merck Manual of Diagnosis and Therapy, Merck Research Laboratories, Rahway, NJ, 16th edition, 1992, pp 138–146.

Goodman and Gilman's The Pharmaceutical Basis of Therapeutics, MacMillan Publishing Co., New York, 7th edition, 1985, pp 1199–1215.

Bennett, J. C., et al., Cecil's Textbook of Medicine, 20th edition, W. B. Saunders Co., Philadelphia, 1996, pp 1683–1691.

* cited by examiner

Primary Examiner—Kevin E. Weddington

(57) ABSTRACT

The present invention provides a method and composition of medications use to treat inflammatory bowel disease. The invention further provides combinations of anti-atypical mycobacterial agents effective against the atypical mycobacterial strains. It also provides a method of potentiating the anti-atypical mycobacterial agents effective agents in treatment of inflammatory bowel disease by immunising patients with extracts of non-pathogenic mycobacteria.

22 Claims, No Drawings

METHODS AND COMPOSITIONS FOR TREATING INFLAMMATORY BOWEL DISEASE

TECHNICAL FIELD

The invention relates to compositions and methods for the treatment of inflammatory bowel disease, such as Crohn's disease.

BACKGROUND OF THE INVENTION

Inflammatory bowel disease (IBD) is a disorder of unknown aetiology characterised typically by diarrhoea, cramping, abdominal pains, weight loss and rectal bleeding. It encompasses such disorders as Crohn's disease, ulcerative colitis, indeterminate colitis, microscopic colitis and collagenous colitis. Its cause is unknown. However, in the past there has been some evidence that *Mycobacterium paratuberculosis* (Mp) and perhaps its various sub-strains, may play an infective role by entering the cells which make up the bowel wall. The source of this bacterium is unclear but may reside in other animals such as sheep, cattle, rabbits, as well as other humans. It may be transmitted to people perhaps via milk, contaminated water supplies, poorly cooked meat, etc. Although there has been long-standing controversy about the involvement of Mp in causation of Crohn's disease, recent applications of PCR usage are beginning to confirm that most Crohn's cases are indeed infected with this organism which is likely to be the causal infective agent. In the past, therapy directed at the eradication of Mp by using combined anti-TB drugs eg INH, pyrazinamide, streptomycin, ethambutol, rifampicin and PAS have been generally of little help to patients. In other words, although transient improvements in a proportion of patients did occur, no patient was cured. In fact, even if Mp had been the cause of this disease there was no effective therapy available for Mp since it was an "atypical mycobacterium" and for atypical mycobacteria there was no known therapy. Furthermore, since *Mycobacterium paratuberculosis* has a long division time multiple antimicrobial drugs are required to the treat the infection which has to be carried out for a long period of time—akin to the treatment used in the therapy of *Mycobacterium tuberculosis*. Furthermore, *Mycobacterium tuberculosis* therapy with the current drugs results in resistant strains forming. Such resistant strains do not become eradicated with known antimicrobial agents. Hence, there is no known effective cure for resistant TB.

Accordingly, there is a need for an effective treatment of inflammatory bowel disease, and in particular Crohn's disease. It is an object of this invention to provide such a treatment.

Surprisingly, the present inventor has discovered that the metabolism of the mycobacteria believed to be responsible for the symptoms of inflammatory bowel disorders may be inhibited long enough to cure the infection and thus relieve the symptoms, by administering to the patient a combination of anti-atypical mycobacterial agents and/or an immunising amount of a mycobacterial product.

SUMMARY OF THE INVENTION

The present invention provides a method and composition of medications used to treat inflammatory bowel disease including Crohn's disease and colitis. The methods of the invention result in a cure of the infection and reversal of the clinical condition. The invention further provides combinations of anti-atypical mycobacterial agents effective against the atypical mycobacterial strains. It also provides a method of potentiating the anti-atypical mycobacterial agents in treatment of inflammatory bowel disease by immunising patients with extracts of non-pathogenic mycobacteria.

Thus, in a first embodiment, the invention provides a composition for the treatment of inflammatory bowel disease including three or more anti-atypical mycobacterial agents.

In a second embodiment, the invention provides a method for the treatment of inflammatory bowel disease including administering to a patient in need of said treatment an effective amount of at least three anti-atypical mycobacterial agents.

In a third embodiment, the invention provides a method for the treatment of inflammatory bowel disease including administering to a patient in need of said treatment an effective amount of at least three anti-atypical mycobacterial agents and immunising the patient with an immunising amount of a mycobacterial extract or product.

In a fourth embodiment, the invention provides a method for the treatment of inflammatory bowel disease including administering to a patient in need of said treatment an immunising amount of a mycobacterial extract or product.

In further embodiments, the invention provides (a) the use of a composition comprising three or more anti-atypical mycobacterial agents for the manufacture of a medicament for the treatment of inflammatory bowel disease; (b) the use of a composition including at least three anti-atypical mycobacterial agents and a mycobacterial extract or product for the manufacture of a medicament for the treatment of inflammatory bowel disease; and (c) the use of a mycobacterial extract or product for the manufacture of a medicament for the treatment of inflammatory bowel disease.

DESCRIPTION OF THE INVENTION

This invention discloses a method of use and compositions useful in the treatment of Crohn's disease and colitis and of other inflammatory bowel diseases using various combinations of anti-atypical mycobacterial drugs.

In the composition of the first embodiment of the invention, or the methods of the second or third embodiments, valid combinations of anti-atypical mycobacterial agents include triple (three drugs) groupings of anti-atypical mycobacterial agents, or indeed larger combinations for exceptional situations, eg where resistant strains emerge. Four, five and even six drug combinations may be required in patients with resistant *Mycobacterium paratuberculosis* strains. Suitable anti-atypical mycobacterial agents include, but are not limited to, clarithromycin, rifabutin, rifampicin, rifapentene, azithromycin, roxithromycin, cefazoline, minocyclin, streptomycin, amikacin, clofazimine, ethambutol, ofloxacin, sparfloxacin, levofloxacin, pefloxacin, grepafloxacin, trovafioxacin, norfloxicin, enoxacin, lomefloxacin, ciprofloxacin and oxazolidinone. These may be co-used with one or more 5-aminosalicylic acid compounds or 4-aminosalicylic acid compounds such as mesalazine, olsalazine, salazopyrin or para-amino salicylic acid. Typically, at least one of the anti-atypical mycobacterial agents is rifabutin or clarithromycin. More typically, the composition of the first embodiment includes rifabutin, clarithromycin and clofazimine. Similarly, the methods of the second and third embodiments usually involve the administration to the patient of an effective amount of a combination of rifabutin, clarithromycin, and clofazimine.

Surprisingly, the combination of three or more anti-atypical mycobacterial agents exhibits a substantially greater effect against inflammatory bowel disease than would have been expected from each anti-atypical mycobacterial agent alone.

Typically, the composition of the present invention may include between 10–500 mg of each of three or more anti-atypical mycobacterial agents. More typically, the composition of the present invention may include between 10–250 mg of each of three or more anti-atypical mycobacterial agents. Even more typically, the composition of the present invention may include rifabutin present at between 50–250 mg, more typically, approximately 15 mg, clarithromycin at between 200–30 mg, more typically, approximately 250 mg, and clofazimine at between 10–150 mg, more typically, approximately 50 mg. Further, other anti-atypical mycobacterial agents may be present in amounts in accordance with known dosages.

Typically, the composition of the present invention may be available in the form of a tablet containing each of three or more anti-atypical mycobacterial agents present in a compressed powdered form. Alternatively, the composition of the present invention may be available in the form of a tablet capsule containing one or more of the anti-atypical mycobacterial agents in a microencapsulated form. As another possibility, the composition of the present invention may be available in the form of a tablet capsule containing one of the three or more anti-atypical mycobacterial agents present in a powdered form, and the remaining anti-atypical mycobacterial agents present in a microencapsulated form. As a further possibility, the composition of the present invention may be available in the form of a tablet capsule containing each of three or more anti-atypical mycobacterial agents present in a microgranulated form. In even further possibilities, the composition of the present invention may be available in the form of a tablet(s) containing one or more of the anti-atypical mycobacterial agents within a capsule, a capsule(s) containing one or more of the anti-atypical mycobacterial agents within a tablet, a capsule(s) containing one or more of the anti-atypical mycobacterial agents within an outer capsule containing the other anti-atypical mycobacterial agents, or any combination of the above.

In a preferred form, the composition of the invention consists of an inner capsule containing rifabutin, within an outer capsule containing clarithromycin and clofazimine, wherein clarithromycin and clofazimine may be present in powdered, microencapsulated, or microgranulated forms.

Typically, the methods of the present invention may be carried out by administration of one or more tablets/capsules containing each of three or more anti-atypical mycobacterial agents as described in the immediately preceding paragraph, or through the administration of each of three or more anti-atypical mycobacterial agents separately.

In the method of the fourth embodiment a patient previously not treated or on current anti-inflammatory therapies is treated by immunisation with a mycobacterial extract or product (living or dead, or its extracted wall and DNA components) as an immunising agent to stimulate leucocytes in the immunised patient. Such immunising agents may be extracts or products from known, non-pathogenic mycobacteria such as M. vaccae or M. phlei. As used herein, the expression "mycobacterial extract or product" means whole killed mycobacteria or mycobacterial extract, with or without adjuvants. An example of a suitable mycobacterial product or extract is Regressin, available from Bioniche of London, Ontario, Canada.

The mycobacterial product may be used to recurrently imunise the patient using the product as an immunostimulant. The mycobacterial product can be administered via any of several routes, such as oral, intravenous, intramuscular or subcutaneous. Such immunisations can rid the patient of the Mp infection and have the ability to cure the disease or place the patient into a prolonged remission. Administration of the mycobacterial product or extract is typically from weekly to monthly, but may be more or less frequent. An appropriate treatment regime may be arrived at readily by a medical practitioner in any particular case, given the teaching herein.

A preferred therapy with *Mycobacterium phlei* extract (eg Regressin) includes a weekly immunisation program, increasing the dosage by 50 $\mu$g of the extract every week until the patient develops fever, rigors and nausea. The dose is then dropped by 50 $\mu$g to the lower level and the patient continues maintenance immunisation on a monthly basis. The treatment can last from 6 weeks up to a monthly immunisation program of 2 years or more.

In another form of therapy standard anti-inflammatory therapy can be combined with recurrent Regressin immunisation.

In the method of the third embodiment, at least three anti-atypical mycobacterial agents are combined with use of a mycobacterial extract or product as an immunising agent. The mycobacterial extract or product for use in the method of the third embodiment may be a mycobacterial extract or product as described above with reference to the third embodiment. For example, rifabutin may be combined with clarithromycin and clofazimine in the therapy and further combined with an immunising protocol using *M. phlei* extract (e.g. Regressin).

In the methods of the invention, the anti-atypical mycobacterial agents are usually used continuously over a period of 3 to 36 months. Dosages of the anti-atypical mycobacterial agents are generally in accordance with known dosage ranges For example, the typical dosage of clarithromycin is from 250 mg to 1.5 g per day, more typically about 750 mg per day; the typical dosage of rifabutin is from 150 mg to 750 mg per day, more typically about 450 mg per day, the typical dosage of clofazimine is from about 1 mg/kg to about 6 mg/kg, more typically about 2 mg/kg; the typical dosage of ethambutol is up to about 15 mg/kg; and the typical dosage of azithromycin is from 250 mg to 1000 mg per day, more typically about 500 mg per day.

The inflammatory process may be monitored by colonoscopy and biopsy, as well as various blood parameters, during the course of treatment in accordance with the invention.

Preferably, the method of the third embodiment consists of a 24 month treatment daily of clarithromycin combined with rifabutin and clofazimine, at dosages as described above. In a more preferred method, the patient will also be recurrently immunised at intervals using a mycobacterial extract of *M. phlei* (Regressin). This can be given orally, intravenously, subcutaneously, or in combinations of the above. Doses of the mycobacterial extract can be given in any frequency ranging from 25 $\mu$g to 500 $\mu$g, more typically, 50 $\mu$g to 500 $\mu$g. However, weekly to monthly, typically weekly or monthly, is usually adequate to maintain immunostimulation.

The methods of the present invention can also be combined with one or more milder anti-TB agents such as salazopyrin, olsalazine or mesalazine, as well as other less known aminosalicylic acids. The 4-aminosalicyclic acids or 5-aminosalicylic acids can be combined with any three or more of the anti-atypical mycobacterial agents mentioned above. Dosages of these agents are generally known. For example the typical dosage range for salazopyrin is in the range of from about 500 mg to 4 g per day; and for olsalazine or mesalazine from about 500 mg to about 3 g per day. Thus, the composition of the first embodiment may further include an agent effective against tuberculosis. Similarly, the method of the second or third embodiments may further include administering an effective amount of an agent effective against tuberculosis.

Compositions for administration of the invention may be prepared by means known in the art for the preparation of compositions (such as in the art of pharmaceutical compositions) including blending, grinding, homogenising, suspending, dissolving, emulsifying, dispersing and where appropriate, mixing of the anti-atypical mycobacterial agent together with selected excipients, diluents, carriers and adjuvants.

For oral administration, the pharmaceutical composition may be in the form of tablets, lozenges, pills, troches, capsules, elixirs, powders, including lyophilised powders, solutions, granules, suspensions, emulsions, syrups and tinctures. Slow-release, or delayed-release, forms may also be prepared, for example in the form of coated particles, multi-layer tablets or microgranules.

Solid forms for oral administration may contain pharmaceutically acceptable binders, sweeteners, disuinegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of to wintergreen, cherry, orange or raspberry flavouring. Suitable coating agents include polymers or copolymers of acrylic acid and/or methacrylic acid and/or their esters, waxes, fatty alcohols, zein, shellac or gluten Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monoslearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further include dispersing agents and/or suspending agents. Suitable suspending agents include sodium carboxymethylcellulose, methylcellulose, hydroxypropylmethyl-cellulose, polyvinyl-pyrrolidone, sodium alginate or ceryl alcohol. Suitable dispersing agents include lecithin, polyoxyechylene esters of fatty acids such as stearic acid, polyoxyethylene sorbitol mono- or di-oleate, -stearate or -laurate, polyoxyethylene sorbitan mono- or-dioleate, -stearate or -laurate and the like.

The emulsions for oral administration may further include one or more emulsifying agents. Suitable emulsifying agents include dispersing agents as exemplified above or natural gums such as gum acacia or gum tragacanth.

EXAMPLES

Example 1

Treatment of patients with inflammatory bowel disease using a combination of anti-atypical mycobacterial agents Fifteen patients, aged 13 to 58, were treated with various protocols of anti-mycobacteria agents. Twelve patients had Crohn's disease and three ulcerative colitis. Presence of *Mycobacterium paratuberculosis* was identified in nine of these patients. A combination of claithromycin (250 mg to 1.5 grams per day), rifabutin (150 mg to 750 mg per day) and clofazimine (3 mg/kg to 10 mg/kg) was used. Rapid clinical remission was obtained in these patients with cessation of prednisone, azathioprine, and 5ASA compounds and settlement clinically of their inflammatory bowel disease.

After four months of treatment, five patients were examined colonoscopically. Two of these patients had normalised the colonic and terminal ileum mucosa while three continued to have patchy inflammatory changes and histological presence of minimal inflammatory infiltrate with some eosinophils.

In these three patients, a combination of clarithromycin and rifabutin (same dosages as above) together with added clofazimine, 2 mg per kg, made up a preferred therapy. Seventy percent of the patients improved dramatically at 8 months with removal of all need for anti-inflammatory bowel disease medications. No prednisone, azathioprine or 5ASA compounds were used. The inflammatory process in these patients was no longer detectable and even histologically no evidence of IBD was present when viewed under the microscope. However, in one patient who was sensitive to rifabutin (marked headaches and fever) the rifabutin was changed to ethambutol at a dose of 400 mg twice daily. This dose was increased at one stage to 50 mg per kg in an attempt to reverse the inflammatory process and then reduced to 10 mg per kg. The patient also obtained reversal of the inflammatory process with loss of diarrhoea, loss of bleeding, and ultimately loss of urgency. In yet a further patient four drugs were used simultaneously because of resistance to clarithromycin. Azithromycin, 500 mg each morning (range 250–1,500 mg) was used in combination with rifabutin, clofazimine, and ethambutol.

Example 2

Treatment of patient with inflammatory bowel disease using a microbial extract

A 34 year old patient with two bowel resections and a stricturotomy while on standard Crohn's disease therapy consisting of azopiathrin, prednisone and mesalazine received an immuno-stimulatory injection of Regressin. This was given intramuscularly and later orally in a starting dose of 500 µg, followed by 500 µg weekly for four weeks, tand hen monthly.

Two years after recurrent oral immunisation on a weekly and then monthly basis, the patient remains symptom-free and off all therapy, suggestive of Crohn's disease reversal and disappearance. At colonoscopy the anastomosis site was free of Crohn's disease.

Example 3

Treatment of Severe Crohn's Disease using Rifabutin-Macrolide-Clofazimine Combination Patients failing maximal conventional therapy were commenced prospectively on a combination of rifabutin (450 mg/day), clarithromycin (750 mg/day), and clofazimine (2 mg/kg). Azathiaprine was terminated while 5-ASA and steroids were tapered then ceased. Progress was monitored by colonoscopy, cross-sectional ultrasound, haematology values and the Harvey-Bradshaw activity index. After 8–12 months, 10 patients achieved near-complete control of Crohn's disease on the combination therapy alone. Ileal structures dilated to normal ultrasound wall thickness in all of the five patients examined. Extensive pseudo polyp crops regressed from the colon in the patient suffering from this condition, defunctioning ileostomy was closed at 11 months in the patient suffering from this condition, reversal from inflamed to histologically uninflamed ileal and colonic mucosa was observed in five of twelve patients suffering from this condition. All patients had essentially normalised haematologic values after 8–12 months of treatment. In 2 patients, Crohn's disease progressed 2–3 months after cessation of steroids which were subsequently reintroduced while continuing the combined therapy of the present invention. The Harvey-Bradshaw index fell from 15.5 to 2.5.

Example 4
Composition for oral administration to patient with inflammatory bowel disease A composition was prepared containing 150 mg Rifabutin, 250 mg Clarithromycin and 50 mg Clofazimine. The composition was presented in the form of a capsule containing each of the anti-atypical mycobacterial agents in a microencapsulated form.

Example 5
Composition for oral administration to patient with inflammatory bowel disease A composition was prepared containing 150 mg Rifabutin, 250 mg Clarithromycin and 50 mg Clofazimine. The composition was presented in the form of an inner capsule containing rifabutin, within an outer capsule containing clarithromycin and clofazimine, wherein clarithromycin and clofazimine are present in powdered form.

Example 6
Composition for oral administration to patient with inflammatory bowel disease A composition was prepared containing 150 mg Rifabutin, 250 mg Clarithromycin and 50 mg Clofazimine. The composition was presented in the form of an inner capsule containing rifabutin, within an outer capsule containing clarithromycin and clofazimine, wherein clarithromycin and clofazimine are present in microgranulated form.

Example 7
Composition for oral administration to patient with inflammatory bowel disease A composition was prepared containing 150 mg Rifabutin, 250 mg Clarithromycin and 50 mg Clofazimine. The composition was presented in the form of an inner capsule containing rifabutin, within an outer capsule containing clarithromycin and clofazimine, wherein clarithromycin and clofazimine are present in microgranulated form.

INDUSTRIAL APPLICABILITY

The present invention provides a method and composition of medications used to treat inflammatory bowel disease. The invention further provides combinations of anti-atypical mycobacterial agents effective against the atypical mycobacterial strains. It also provides a method of potentiating the anti-atypical mycobacterial agents in treatment of inflammatory bowel disease by immunising patients with extracts of non-pathogenic mycobactcria.

What is claimed is:

1. A composition for the treatment of inflammatory bowel disease comprising three or more anti-atypical mycobacterial agents, wherein at least one of said agents is a macrolide.

2. The composition of claim 1, wherein said anti-atypical mycobacterial agents are selected from the group consisting of: clarithromycin, rifabutin, rifampicin, azidiromycin, roxithromycin, amikacin, clofazimine, ethambutol, ofloxacin, ciprofloxacin and oxazolidinone.

3. The composition of claim 1, comprising rifabutin and clarithromycin.

4. The composition of claim 1, comprising rifabutin, clarithromycin and clofazimine.

5. The composition of claim 1, further comprising at least one 5-aminosalicylic acid compound or 4-aminosalicylic acid compound.

6. The composition of claim 5, wherein said 5-aminosalicylic acid compound or 4-aminosalicylic acid compound is selected from the group consisting of mesalazine, olsalazine, salazopyrin and para-amino salicylic acid.

7. A method for the treatment of inflammatory bowel disease comprising administering to a patient in need of said treatment an effective amount of at least three anti-atypical mycobacterial agents, wherein at least one of said agents is a macrolide.

8. The method of claim 7 which additionally comprises immunizing the patient with a immunizing amount of a mycobacterial extract or product.

9. The method of claim 7 or 8, wherein said anti-atypical mycobacterial agents are selected from the group consisting of: clarithromycin, rifabutin, rifampicin, azithrotnycin, roxithromycin, amikacin, clofazimine, ethambutol, ofloxacin, ciprofloxacin and oxazolidinone.

10. The method of claim 7 or 8, comprising administering to said patient rifabutin and clarithromycin.

11. The method of claim 7 or 8, comprising administering to said patient rifabutin, clarithromycin and clofazimine.

12. The method of claim 7 or 8, comprising administering to said patient at least one 5-aminosalicylic acid compound or 4-aminosalicylic acid compound.

13. The method of claim 12, wherein said 5-aminosalicylic acid compound or 4-aminosalicylic acid compound is selected from the group consisting of: mesalazine, olsalazine, salazopyrin and para-amino salicylic acid.

14. The method of claim 8, wherein said mycobacterial extract or product comprises an extract or product from non-pathogenic mycobacteria.

15. The method of claim 14, wherein said non-pathogenic bacteria comprise *M vaccae* or *M phlei*.

16. The method of claim 8, wherein said amount of a mycobacterial extract or product ranges from between about 25 $\mu$g to about 500 $\mu$g.

17. The method of claim 8, wherein said mycobacterial extract or product is administered orally, intravenously, intramuscularly, subcutaneously, or any combination thereof.

18. The method of claim 8, wherein said immunizing amount of a mycobacterial extract or product is administered from weekly to monthly.

19. The method of claim 8, wherein said immunizing amount of a mycobacterial extract or product is administered weekly.

20. The method of claim 8, wherein said mycobacterial extract or product is Regressin.

21. The composition of claim 1, wherein the macrolide is selected from the group consisting of clarithromycin, azithromycin and roxithromycin.

22. The method of claim 7, wherein the macrolide is selected from the group consisting of clarithromycin, azithromycin and roxithromycin.

* * * * *